(12) United States Patent
Mangual-Soto et al.

(10) Patent No.: US 11,648,404 B2
(45) Date of Patent: May 16, 2023

(54) METHOD AND DEVICE FOR DESIGNATING LEFT VENTRICULAR PACING BASED ON PRE-LV AND POST-LV PACING CARDIAC ACTIVITY SIGNALS

(71) Applicant: Pacesetter, Inc., Sylmar, CA (US)

(72) Inventors: Jan O. Mangual-Soto, Rho (IT); Nima Badie, Berkeley, CA (US); Luke C. McSpadden, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 155 days.

(21) Appl. No.: 17/064,961

(22) Filed: Oct. 7, 2020

(65) Prior Publication Data
US 2022/0105345 A1 Apr. 7, 2022

(51) Int. Cl.
*A61N 1/368* (2006.01)
*A61N 1/37* (2006.01)
*A61N 1/365* (2006.01)

(52) U.S. Cl.
CPC .......... *A61N 1/3682* (2013.01); *A61N 1/365* (2013.01); *A61N 1/371* (2013.01)

(58) Field of Classification Search
CPC ... A61N 1/371; A61N 1/3712; A61N 1/36843
See application file for complete search history.

(56) References Cited

U.S. PATENT DOCUMENTS

| 7,684,863 B2 | 3/2010 | Parikh et al. |
| 10,086,206 B2 | 10/2018 | Sambelashvili |
| 2015/0246235 A1* | 9/2015 | Ghosh ............ A61B 5/35 607/28 |

\* cited by examiner

Primary Examiner — George R Evanisko
(74) Attorney, Agent, or Firm — The Small Patent Law Group LLC; Dean D. Small

(57) ABSTRACT

A system and method for designating between types of activation by a pulse generator configured to deliver a left ventricular (LV) pacing pulse at an LV pacing site as part of a cardiac resynchronization therapy (CRT) are provided. The system includes a sensing channel configured to collect cardiac activity (CA) signals along at least one sensing vector extending through a septal wall between the LV and right ventricle (RV). The CA signals are indicative of one or more beats and include a pre-LV pacing segment indicative of cardiac activity preceding the LV pacing pulse and a post-LV pacing segment indicative of cardiac activity following the LV pacing pulse. The system includes memory to store program instructions. One or more processors are configured to implement the program instructions to analyze the pre-LV pacing segment to identify a first myocardium activation (MA) characteristic of interest (COI). The system analyzes the post-LV pacing segment to a second MA COI, compares the first and second MA COI to first and second MA criteria, respectively, designates the CA signals to be indicative of one of a fusion beat, a capture beat or a pseudofusion beat based on the comparison of the first and second MA COI to first and second MA criteria and store a result of the designation.

23 Claims, 9 Drawing Sheets

METHOD AND DEVICE FOR DESIGNATING LEFT VENTRICULAR PACING BASED ON PRE-LV AND POST-LV PACING CARDIAC ACTIVITY SIGNALS

BACKGROUND

Embodiments of the present disclosure generally relate to methods and devices for monitoring left ventricular (LV) pacing, and more particularly for designating between fusion, capture and pseudo-fusion LV pacing based on pre-LV and post-LV pacing cardiac activity signals.

Cardiac resynchronization therapy (CRT) seeks to normalize asynchronous cardiac electrical activation and resultant asynchronous contractions associated with congestive heart failure (CHF) by delivering synchronized pacing stimulus to both ventricles of the heart. The stimulus is synchronized to improve overall cardiac function and reduce the susceptibility to life-threatening tachyarrhythmias. CRT may involve pacing from the right ventricular (RV) apex, the transvenous LV (e.g., in the lateral or postero-lateral vein), and the right atrium (RA). Studies have suggested that biventricular (BiV) pacing from two LV sites results in a further improved clinical outcome in CRT patients, in comparison with conventional BiV pacing.

CRT has become the standard of care for patients with chronic heart failure (HF) and reduced ejection fraction (EF) that do not respond to pharmacological treatment. Adequate device programming is important to maintain consistent and effective myocardial capture and delivered therapy. Pseudofusion of the pacing impulse with an existing activation wavefront results in ineffective myocardial capture. Inappropriate atrioventricular (AV) and right ventricular-left ventricular (VV) delay programming, or changes in intrinsic conduction timing, can result in pseudofusion and ineffective therapy. This is particularly important during AF episodes, in which irregularity in AV conduction can lead to as much as 20% of beats being pseudofusion, reducing patient response to CRT.

Different myocardial activation mechanisms can be observed during left ventricle (LV) only pacing in CRT. For example, effective LV capture occurs when the myocardium at the LV pacing electrode is activated solely by the impulse initiated at the LV pacing electrode. Fusion pacing occurs when myocardium at the LV pacing electrode is activated by a combination of the impulse initiated at the LV pacing electrode and a concurrent activation wavefront that originated remotely (e.g., intrinsic wavefront originating at the sinus node). Pseudofusion occurs when the myocardium at the LV pacing electrode is activated by an activation wavefront that originated remotely, ineffective LV pacing occurs during the myocardial refractory period (non-capture).

An opportunity remains to improve upon differentiation between the various types of myocardial activation and to improve upon tracking an effectiveness of CRT.

SUMMARY

In accordance with embodiments herein, a system for designating between types of activation by a pulse generator configured to deliver a left ventricular (LV) pacing pulse at an LV pacing site as part of a cardiac resynchronization therapy (CRT) is provided. The system includes a sensing channel configured to collect cardiac activity (CA) signals along at least one sensing vector extending through a septal wall between the LV and right ventricle (RV). The CA signals are indicative of one or more beats. The CA signals include a pre-LV pacing segment indicative of cardiac activity preceding the LV pacing pulse and a post-LV pacing segment indicative of cardiac activity following the LV pacing pulse. The system includes memory to store program instructions. One or more processors are configured to implement the program instructions to analyze the pre-LV pacing segment to identify a first myocardium activation (MA) characteristic of interest (COI). The system analyzes the post-LV pacing segment to a second MA COI, compares the first and second MA COI to first and second MA criteria, respectively, designates the CA signals to be indicative of one of a fusion beat, a capture beat or a pseudofusion beat based on the comparison of the first and second MA COI to first and second MA criteria and store a result of the designation.

Optionally, the first MA COI may be indicative of whether LV tissue proximate to the LV pacing site is in a state that is responsive to the LV pacing pulse. The one or more processors may analyze the pre-LV pacing segment of the CA signals to identify, as the first MA COI, at least one of a baseline voltage or baseline slope. The one or more processors may be configured to compare the at least one of the baseline voltage or baseline slope to a corresponding baseline voltage range or baseline slope range which represents the first MA criteria. At least one of the baseline voltage range or baseline slope range may define a limit in order for LV tissue proximate to the LV pacing site to be in a non-refractory state. The one or more processors may be configured to designate the CA signals as a pseudofusion beat when the comparison of the first MA COI to the first MA criteria indicates that the LV tissue is in a refractory state that is nonresponsive to the LV pacing pulse.

Optionally, the one or more processors may be configured to designate the CA signals as at least one of a capture beat or a fusion beat when the comparison of the first MA COI to the first MA criteria indicates that the LV tissue is in a non-refractory state that is responsive to the LV pacing pulse. The second MA COI may be indicative of whether the LV pacing pulse achieved capture or fusion. The one or more processors may be configured to analyze the post-LV pacing segment of the CA signals to identify, as the second MA COI, a sign of an initial slope of an evoked response (ER) that is responsive to the LV pacing pulse. The one or more processors may be configured to designate the CA signals as a fusion beat when the sign of the initial slope is positive and to designate the CA signals as a capture beat when the sign of the initial slope is negative. The one or more processors may be configured to identify the sign of a peak in the initial slope, and to designate the CA signals as a pseudofusion beat when no peak is identified in the post-LV pacing segment of the CA signals.

Optionally, the memory may be configured to store at least one of: i) a histogram indicating a relation between a number of beats during which LV pacing was delivered and a number of the beats for which the LV pacing was effective to achieve at least one of capture or fusion; ii) a log of at least one of a number of capture beats, number of fusion beats or number of pseudofusion beats; iii) a log of a percentage of a total number of LV paced beats for which the LV pacing pulses achieved capture; iv) a log of a percentage of a total number of LV paced beats for which the LV pacing pulses achieved fusion; or v) a log of a percentage of a total number of LV paced beats for which the LV pacing pulses achieved pseudofusion. The system may include an implantable medical device that includes the pulse generator configured to deliver the CRT. The one or more processors and the memory may configure to adjust at least one of an atrial-ventricular delay or a ventricular ventricular delay parameter utilized by the CRT when a count of pseudofusion beats exceeds a threshold.

In accordance with embodiments, a method for designating between types of activation in connection with cardiac resynchronization therapy (CRT) that includes delivery of an LV pacing pulse at an LV pacing site is provided. The method is under control of one or more processors within an implantable medical device (IMD). The method collects cardiac activity (CA) signals along at least one sensing vector extending through a septal wall between the LV and right ventricle (RV). The CA signals are indicative of one or more beats. The CA signals include a pre-LV pacing segment indicative of cardiac activity preceding the LV pacing pulse and a post-LV pacing segment indicative of cardiac activity following the LV pacing pulse. The method analyzes the pre-LV pacing segment to identify a first myocardium activation (MA) characteristic of interest (COI). The method analyzes the post-LV pacing segment to a second MA COI, compares the first and second MA COI to first and second MA criteria, respectively. The method designates the CA signals to be indicative of one of a fusion beat, a capture beat or a pseudofusion beat based on the comparison of the first and second MA COI to first and second MA criteria and stores a result of the designating.

Optionally, the first MA COI may be indicative of whether LV tissue proximate to the LV pacing site is in a state that is responsive to the LV pacing pulse. The analyzing the pre-LV pacing segment of the CA signals may include identifying, as the first MA COI, at least one of a baseline voltage or baseline slope and the comparing may include comparing the at least one of the baseline voltage or baseline slope to a corresponding baseline voltage range or baseline slope range which represents the first MA criteria. At least one of the baseline voltage range or baseline slope range may define a limit in order for LV tissue proximate to the LV pacing site to be in a non-refractory state. The designating may include designating the CA signals as a pseudofusion beat when the comparison of the first MA COI to the first MA criteria indicates that the LV tissue is in a refractory state that is nonresponsive to the LV pacing pulse and designating the CA signals as at least one of a capture beat or a fusion beat when the comparison of the first MA COI to the first MA criteria indicates that the LV tissue is in a non-refractory state that is responsive to the LV pacing pulse.

Optionally, the second MA COI may be indicative of whether the LV pacing pulse achieved capture or fusion. The analyzing may include analyzing the post-LV pacing segment of the CA signals to identify, as the second MA COI, a sign of an initial slope of an evoked response (ER) that is responsive to the LV pacing pulse. The designating may include designating the CA signals as a fusion beat when the sign of the initial slope is positive and to designate the CA signals as a capture beat when the sign of the initial slope is negative.

Optionally, the method may deliver the CRT utilizing LV only pacing. The method may store at least one of: i) a histogram indicating a relation between a number of beats during which LV pacing was delivered and a number of the beats for which the LV pacing was effective to achieve at least one of capture or fusion; ii) a log of at least one of a number of capture beats, number of fusion beats or number of pseudofusion beats; iii) a log of a percentage of a total number of LV paced beats for which the LV pacing pulses achieved capture; iv) a log of a percentage of a total number of LV paced beats for which the LV pacing pulses achieved fusion; or v) a log of a percentage of a total number of LV paced beats for which the LV pacing pulses achieved pseudofusion. The method may adjust at least one of an atrial-ventricular delay or a ventricular ventricular delay parameter utilized by a cardiac resynchronization therapy (CRT) when a count of pseudofusion beats exceeds a threshold.

DETAILED DESCRIPTION

Figure 1:
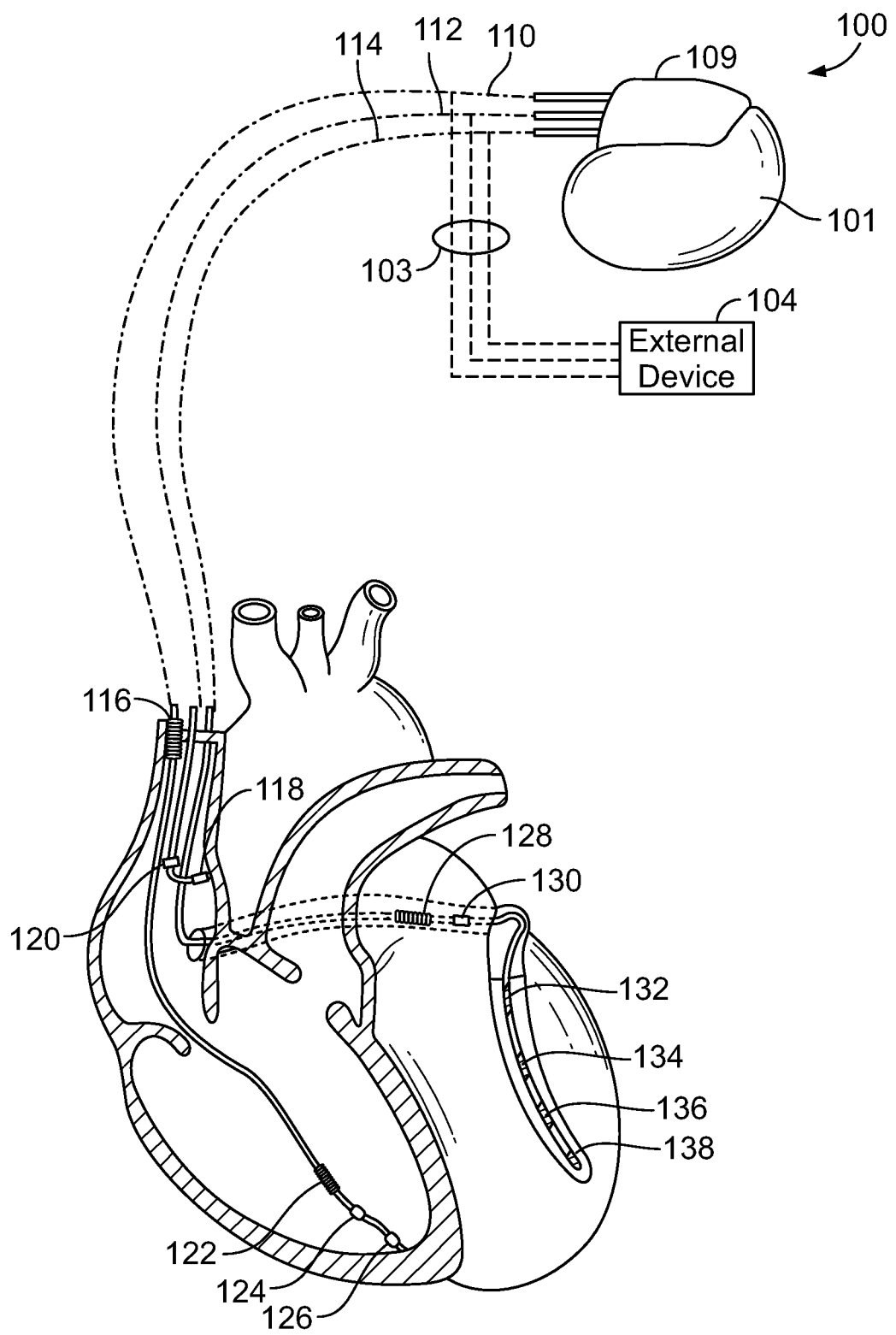
FIG. 1 illustrates an IMD and external device coupled to a heart in a patient and implemented in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The terms "capture", "LV capture" and "effective LV capture", shall mean a type of myocardial activation in which the myocardium at the LV pacing electrode was activated only and solely by the pacing pulse/impulse initiated at the LV pacing electrode and was not concurrently activated by a wavefront that originated remotely. For the avoidance of doubt, the capture, LV capture and effective LV capture type shall mean that the myocardium was not wholly or partially initiated by an intrinsic wavefront originating at the sinus node, nor by an evoked response (ER) wavefront originating at an atrial or HIS pacing electrode.

The terms "fusion", and "LV fusion", shall mean a type of myocardial activation in which the myocardium at the LV pacing electrode is activated by a combination of the pacing pulse/impulse initiated at the LV pacing electrode and a concurrent activation wavefront that originated remotely. For the avoidance of doubt, the fusion and LV fusion type of MA shall mean that the myocardium was partially activated by an intrinsic wavefront originating at the sinus node or an ER wavefront originating at an atrial or HIS pacing electrode.

The term "pseudofusion" shall mean a type of myocardial activation in which the myocardium at the LV pacing electrode is activated only and solely by an activation wavefront that originated remotely and was not concurrently activated by a pacing pulse/impulse at the LV pacing electrode. For the avoidance of doubt, the pseudofusion type of MA shall mean that LV pacing was ineffective and did not achieve capture, such as when LV pacing occurs during the myocardial refractory period.

The term "pre-LV" shall mean a period of time that immediately precedes a scheduled LV pacing event. A start time of a pre-LV window may be based on a scheduled time at which a next LV pacing event will be delivered if no intrinsic LV event occurs and/or based on a time at which an intrinsic or paced atrial event occurred. For example, a pre-LV window shall mean a window of time that begins 5-100 ms, and more preferably, 10-50 ms, prior to a scheduled time of an LV pacing event. The pre-LV window may have a duration that continues up until the time that the LV pacing event or an intrinsic LV event occurs. For example, the pre-LV window may be 5-100 ms, and more preferably 10-50 ms in length.

The term "post-LV pacing" shall mean a period of time that follows an LV pacing event. A post-LV window may be started immediately following delivery of the LV pacing pulse and/or started a predetermined period of time after the LV pacing pulse is delivered. For example, a post-LV window shall mean a window of time that begins 5-25 ms, and more preferably, 20-25 ms, after the LV pacing event. The post-LV window shall have a predetermined or automatically defined duration. For example, the post-LV window may have a length of 100-150 ms, and more preferably 120-130 ms.

The term "LV only" shall mean that no pacing pulse is delivered in the right ventricle. For example, LV only pacing shall include a pacing pulse delivered in or proximate to the left ventricle following an intrinsic atrial event or paced atrial event.

System Overview

Embodiments may be implemented in connection with one or more implantable medical devices (IMDs). Non-limiting examples of IMDs include one or more of implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in: U.S. Pat. No. 9,216,285 "Leadless Implantable Medical Device Having Removable And Fixed Components"; U.S. Pat. No. 8,391,980 "Method And System For Identifying A Potential Lead Failure In An Implantable Medical Device"; U.S. Pat. No. 9,232,485 "System And Method For Selectively Communicating With An Implantable Medical Device"; U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application having Docket No. A15E1059, U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Additionally or alternatively, embodiments herein may be implemented in connection with the methods and systems described in U.S. Pat. No. 10,569,091, titled "Method and Device for Discrimination of Left Ventricular Pseudo-Fusion Pacing", Issue date Feb. 25, 2020; U.S. Publication No. 2017/0216599, titled "Method and System for Adaptive BiVentricular Fusion Pacing", publication date Aug. 3, 2017; U.S. application Ser. No. 16/930,791, titled "Methods, Devices and Systems for Holistic Integrated Healthcare Patient Management", filing date Jul. 16, 2020; U.S. patent application Ser. No. 16/871,166, titled "Systems and Methods for Improved HIS Bundle and Backup Pacing Timing", filing date May 11, 2020, which are incorporated by reference in their entireties.

In accordance with new and unique aspects herein, methods and systems have been developed that identify a unique combination of myocardium activation (MA) characteristics of interest (COI) and apply the MA COI to a unique combination of criteria to readily and efficiently differentiate between different types of myocardial activation, namely to differentiate between effective LV capture, fusion pacing and pseudofusion pacing. Embodiments herein may be implemented as a monitoring device that does not delivery therapy, but collects CA signals from implanted electrodes. The monitoring device may be entirely implanted subcutaneously, but outside of the myocardium, with subcutaneous electrodes located within or outside the myocardium. Optionally, the monitoring device may be implanted entirely within the LV or within a vessel located along the LV. The monitoring device may operate in a coordinated manner with a separate implantable medical device that is configured to deliver the CRT with LV and RV pacing or with LV only pacing. For example, a transvenous IMD system may already be implanted, but later an implantable cardiac monitor may be implanted to designate between fusion, capture and pseudofusion beats.

Additionally or alternatively, the functionality herein maybe added to an IMD, configured to deliver CRT, after the IMD is implanted. For example, the functionality herein may be downloaded to an IMD through a wireless communications link such as over a Bluetooth low energy (BLE) link with an external device (e.g., smart phone, bedside monitor, tablet device, portable or desktop computer, physician programmer).

FIG. 1 illustrates an IMD 100 and external device 104 coupled to a heart in a patient and implemented in accordance with one embodiment. The external device 104 may be a programmer, an external defibrillator, a workstation, a portable computer, a personal digital assistant, a cell phone, a bedside monitor, and/or the like. The IMD may represent a cardiac monitoring device, pacemaker, cardioverter, cardiac rhythm management device, defibrillator, neurostimulator, leadless monitoring device, leadless pacemaker, and/or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as LVD1, LVM2, LVM3 and LVP4) to form a multi-site LV (MSLV) electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

Optionally, the RV lead 110 may be omitted entirely in configurations that implement LV only pacing through the coronary sinus lead 114.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and then transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
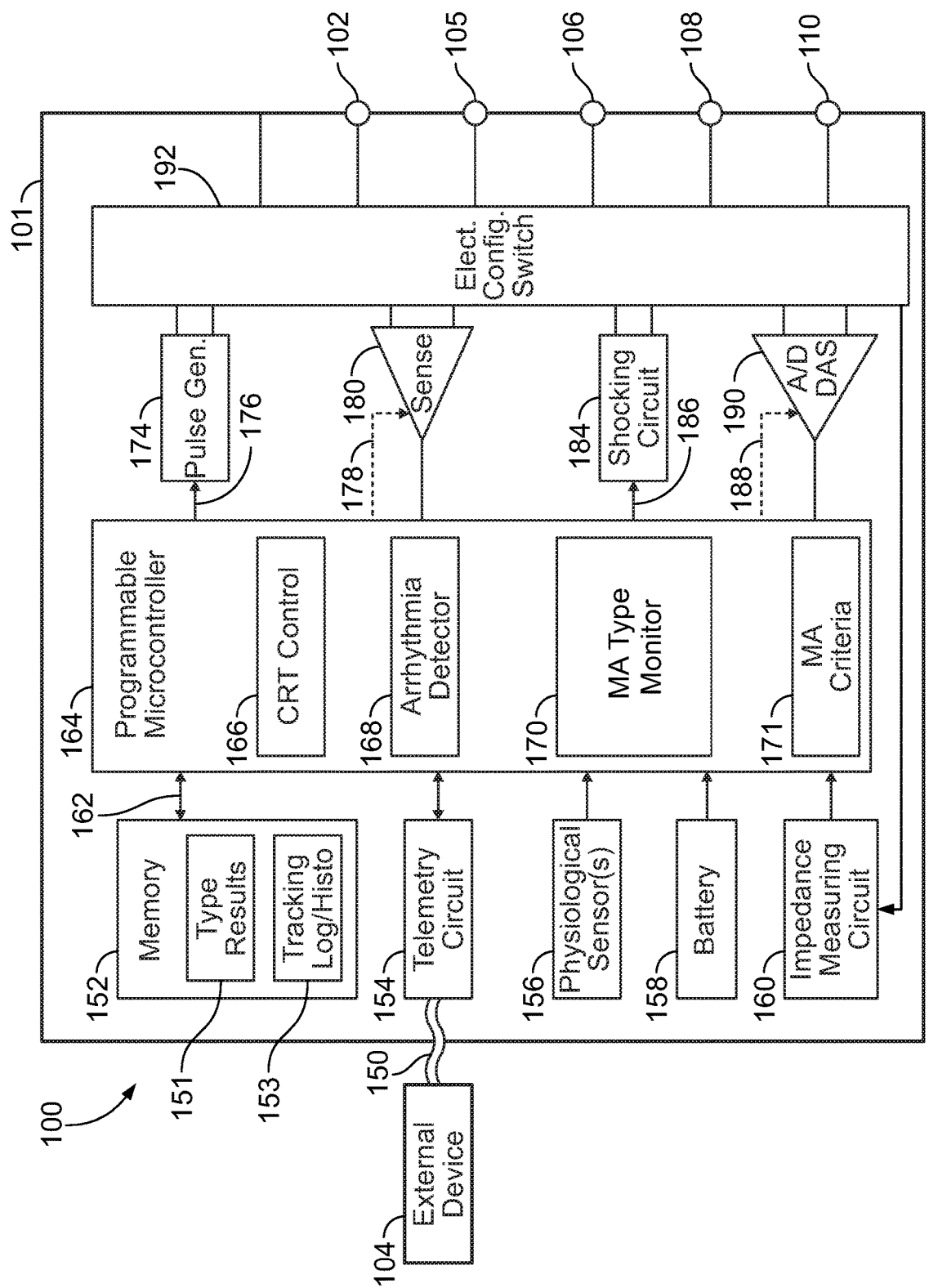
FIG. 2 shows an exemplary IMD that is implanted into the patient as part of the implantable cardiac system in accordance with embodiments herein.

FIG. 2 shows an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. Housing 101 further includes a connector (not shown) with a plurality of terminals 102, 105, 106, 108, and 110. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 110 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes one or more processors (or equivalent control circuitry) that are configured to implement program instructions stored in the memory 152, RAM and/or ROM memory, logic and timing circuitry, state machine circuitry, and I/O circuitry. The one or more processors of the microcontroller 164 implement the program instructions to perform the functionality described in connection with the various blocks or modules illustrated and described within the microcontroller 164 (e.g., blocks 166-171).

IMD 100 further includes a first chamber pulse generator 174 that generates stimulation pulses for delivery by one or more electrodes coupled thereto. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164.

In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

Microcontroller 164 is illustrated to include a CRT control 166 to control the timing of the stimulation pulses (e.g., pacing rate, atrio-ventricular (AV) delay, atrial interconduction (A-A) delay, or ventricular interconduction (V-V) delay, etc.). The CRT control 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions. The CRT control 166 may implement one or more processors to adjust at least one of an atrial-ventricular delay or a ventricular ventricular delay parameter utilized by the CRT when a count of pseudofusion beats exceeds a threshold. In accordance with embodiments, the CRT control 166 manages the pulse generator 174 to deliver a CRT that utilizes LV only pacing, namely pacing at one or more LV pacing sites with no pacing at any RV site. The LV only pacing may be implemented in combination with atrial pacing or without atrial pacing.

Although not shown, the microcontroller 164 may further include other dedicated circuitry and/or firmware/software components that assist in monitoring various conditions of the patient's heart and managing pacing therapies.

The IMD 100 includes sensing circuitry 180 selectively coupled to one or more electrodes that perform sensing operations, through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 192 determines the sensing polarity of the cardiac signal by selectively closing the appropriate switches. In this way, the clinician may program the sensing polarity independent of the stimulation polarity.

The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration.

The IMD 100 further includes an analog-to-digital (ND) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. CRT and operating parameters define, for example, paced event amplitude, pulse duration, electrode polarity, rate, sensitivity, automatic features, arrhythmia detection criteria, and the amplitude, wave shape and vector of each shocking pulse to be delivered to the patient's heart. The operating parameters of the IMD 100 may be non-invasively programmed into the memory 152 through a telemetry circuit 154 in telemetric communication via communication link 150 (e.g., MICS, Bluetooth, or other link) with the external device 104. The telemetry circuit 154 allows intracardiac electrograms and status information relating to the operation of the IMD 100 (as contained in the microcontroller 164 or memory 152) to be sent to the external device 104 through the established communication link 150. The memory 152 also stores morphology templates 151 and conduction pattern templates 153 that are used in accordance with embodiments herein to identify and designate pseudo-fusion.

The IMD 100 can further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. While shown as being included within the unit 100, the physiologic sensor(s) 156 may be external to the IMD 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries.

The IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used.

The microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD 100, as the various slave pacing units described below will typically not be configured to deliver high voltage shock pulses.

The microcontroller 164 further includes an MA type monitor 170 configured to implement the program instructions to analyze the pre-LV pacing segment to identify a first myocardium activation (MA) characteristic of interest (COI); analyze the post-LV pacing segment to a second MA COI; compare the first and second MA COI to first and second MA criteria, respectively; designate the CA signals to be one of a fusion beat, a capture beat or a pseudofusion beat based on the comparison of the first and second MA COI to first and second MA criteria. The microcontroller 164 and/or memory 152 is further configured to maintain multiple MA criteria 171, including at least first and second MA criteria. The first MA COI is indicative of whether LV tissue proximate to the LV pacing site is in a state that is responsive to the LV pacing pulse. The second MA COI is indicative of whether the LV pacing pulse achieved capture or fusion.

The MA monitor 170 is configured to analyze the pre-LV pacing segment of the CA signals to identify, as the first MA COI, at least one of a baseline voltage or baseline slope, the one or more processors configured to compare the at least one of the baseline voltage or baseline slope to a corresponding baseline voltage range or baseline slope range which represents the first MA criteria. Additionally or alternatively, at least one of the baseline voltage range or baseline slope range define a limit in order for LV tissue proximate to the LV pacing site to be in a non-refractory state. Additionally or alternatively, the MA monitor 170 may implement one or more processors to designate the CA signals as a pseudofusion beat when the comparison of the first MA COI to the first MA criteria indicates that the LV tissue is in a refractory state that is nonresponsive to the LV pacing pulse. Additionally or alternatively, the MA monitor 170 may implement one or more processors to designate the CA signals as at least one of a capture beat or a fusion beat when the comparison of the first MA COI to the first MA criteria indicates that the LV tissue is in a non-refractory state that is responsive to the LV pacing pulse.

Additionally or alternatively, the MA monitor 170 may implement one or more processors to analyze the post-LV pacing segment of the CA signals to identify, as the second MA COI, a sign of an initial slope of an evoked response (ER) that is responsive to the LV pacing pulse. Additionally or alternatively, the MA monitor 170 may implement one or more processors to designate the CA signals as a fusion beat when the sign of the initial slope is positive and to designate the CA signals as a capture beat when the sign of the initial slope is negative. Additionally or alternatively, the MA monitor 170 may implement one or more processors to identify the sign of a peak in the initial slope, and to designate the CA signals as a pseudofusion beat when no peak is identified in the post-LV pacing segment of the CA signals.

The memory 152 is configured to store type results 151 of the designation of the CA signals to be one of the fusion beat, capture beat or pseudofusion beat. The memory 152 is further configured to store a log/histogram 153 that includes at least one of: i) a histogram indicating a relation between a number of beats during which LV pacing was delivered and a number of the beats for which the LV pacing was effective to achieve at least one of capture or fusion; ii) a log of at least one of a number of capture beats, number of fusion beats or number of pseudofusion beats; iii) a log of a percentage of a total number of LV paced beats for which the LV pacing pulses achieved capture; iv) a log of a percentage of a total number of LV paced beats for which the LV pacing pulses achieved fusion; or v) a log of a percentage of a total number of LV paced beats for which the LV pacing pulses achieved pseudofusion.

While the block diagram of FIG. 2 illustrates a single IMD that includes all CRT functionality and all monitoring functionality, it is understood that all or a part of the CRT functionality may be implemented in one IMD while all or a part of the monitoring functionality may be implemented in a second IMD. For example, a patient may have a transvenous IMD system that is configured to deliver a CRT. A separate implantable cardiac monitor (ICM) may be implanted in the patient's pectoral area, with the ICM configured to communicate with the CRT type IMD. The CRT type IMD may simply stream CA signals to the ICM, where the CA signals are collected along at least one sensing vector extending through a septal wall between the LV and the RV. The CRT type IMD may deliver LV only or RV-LV based CRT therapy. The ICM may analyze the CA signals as described herein to identify pre-and post-LV pacing segments, to identify the first and second MA COI there from. The ICM may further designate the CA signals to be indicative of one of a fusion, capture or pseudofusion. The ICM may then store the results in the various manners described herein.

As another option, multiple leadless IMD's may be utilized that communicate with one another to provide the CRT functionality and the monitoring functionality described herein.

Process to Track Mechanical Activation Types During LV Pacing

Figure 3A:
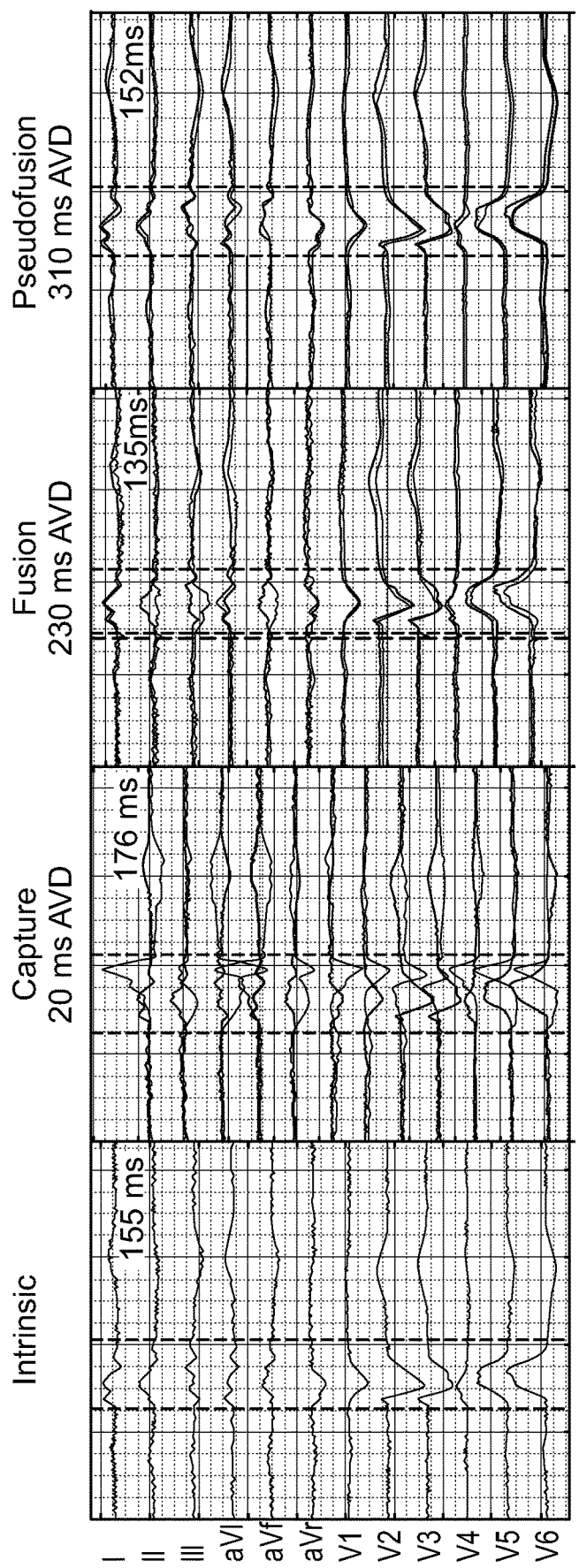
FIG. 3A illustrate examples of CA signals collected by a 12-lead surface ECG during various pacing scenarios in accordance with embodiments herein.
Figure 3B:
FIG. 3B illustrate examples of CA signals collected by an IMD along an LV-RV transverse sensing vector during the same pacing scenarios as in FIG. 3A in accordance with embodiments herein.

FIG. 3A illustrate examples of CA signals collected by a 12 lead surface ECG during various pacing scenarios. FIG. 3B illustrate examples of CA signals collected by an IMD along an LV-RV transverse sensing vector during the same pacing scenarios as in FIG. 3A. The CA signals within the first vertical column, of FIGS. 3A and 3B, correspond to intrinsic conduction in which no LV pacing is utilized. The CA signals within the second vertical column correspond to LV only pacing that achieved LV capture (e.g., when utilizing a short AVD). The CA signals within the third vertical column correspond to LV only pacing that achieved LV fusion (e.g., utilizing an AVD close to the intrinsic A-LV conduction interval). The CA signals within the fourth vertical column correspond to LV only pacing that resulted in LV pseudofusion (e.g., utilizing an AVD slightly longer than the intrinsic A-LV conduction interval). Each of the vertical panels also include dashed vertical lines designate QRS start/end, and QRS durations. In connection with the 12 lead surface ECG of FIG. 3A, light gray ECG lines are superimposed over the CA signals in the second, third and fourth columns corresponding to the capture, fusion and pseudofusion results. The light gray ECG lines correspond to the intrinsic ECG.

In accordance with new and unique aspects herein, it has been determined that capture, fusion, and pseudofusion can be differentiated from one another based on characteristics of interest within the CA signals collected by the IMD when utilizing an LV-RV transverse sensing vector. The characteristics of interest are indicative of differences within the myocardial activation mechanism (MAM). For example, the LV-RV transverse sensing vector may utilize an LV electrode as a cathode and the RV coil as an anode. As explained herein, the MAM COI within the CA signals that facilitate differentiation between capture, fusion and pseudofusion include: 1) baseline voltage pre-pacing, 2) baseline dV/dt pre-pacing, and 3) dV/dt signal peak post-pacing, and the like. Based on the differences between the MAM Cal, embodiments herein are able to identify the type of pacing that is achieved based on the intracardiac electrograms (IEGMs) recorded by the IMD (e.g., a CRT device).

Figure 4A:
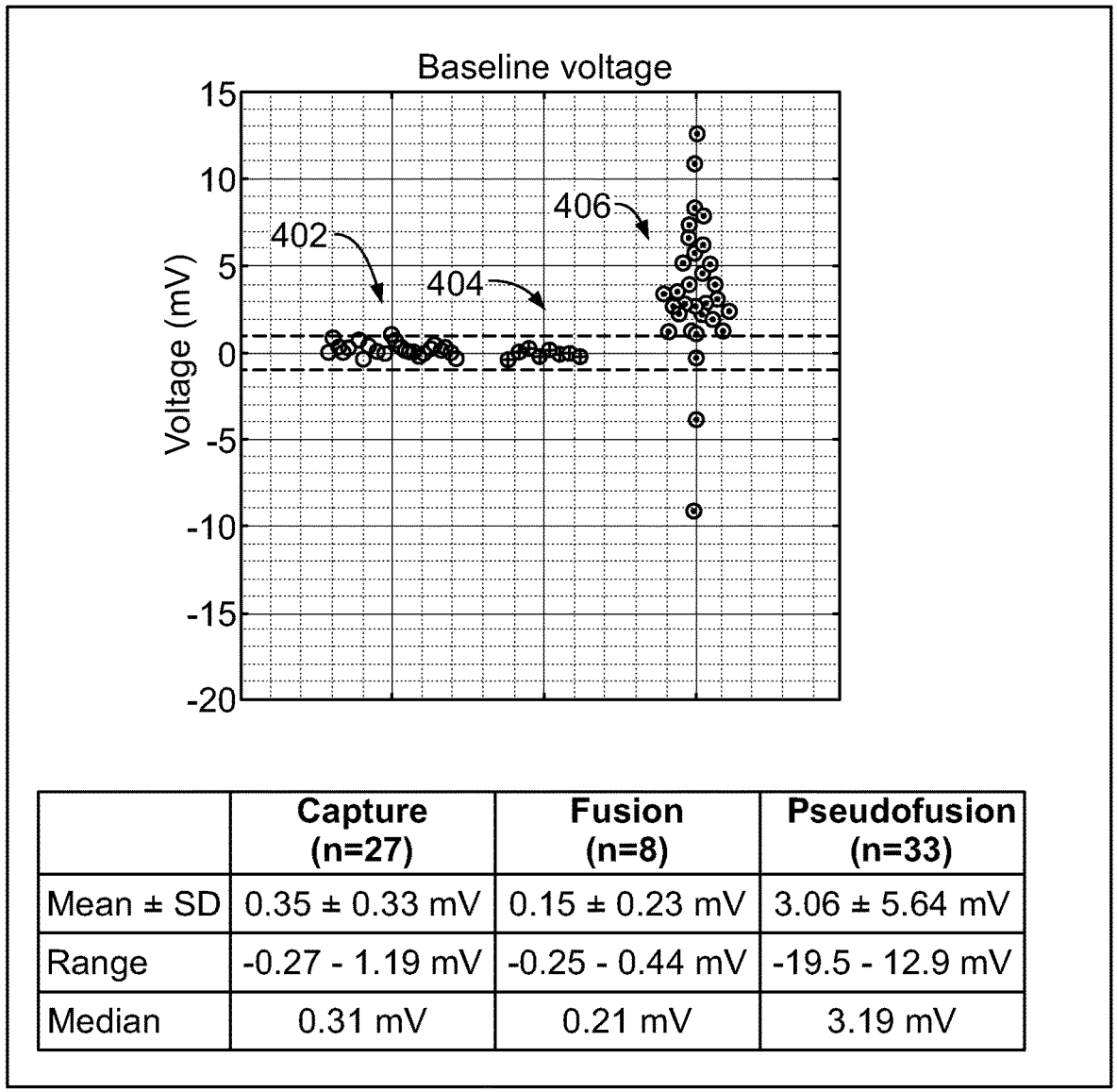
FIG. 4A illustrates a plot of values measured for baseline voltage experienced during a pre-pacing window for collections of heart beats associated with the various types of myocardial activation in accordance with embodiments herein.

FIG. 4A illustrates a plot of values measured for baseline voltage experienced during a pre-pacing window for collections of heart beats associated with the various types of myocardial activation. The points in FIG. 4A may represent data collected from a group of patients who exhibited different types myocardial activation, namely 27 patients exhibited LV capture, 8 patients exhibited fusion and 33 patients exhibited pseudo fusion. Each point in FIG. 4A corresponds to a single heartbeat or an ensemble of heart beats exhibiting a common MA. For example, in FIG. 4A, the group 402 represents a sub-collection of heart beats/ensembles during which the patients experience LV capture, following a corresponding group of LV paced events. The group 404 represents a sub-collection of heart beats/ensembles during which the patients experienced fusion following a corresponding group of LV paced events, and the group 406 represents a sub-collection of heart beats/ensembles during which the patients experienced pseudofusion, following a corresponding group of LV paced events.

A table is presented below the baseline voltage plot of FIG. 4A. In the example dataset of FIG. 4A, a data point may represent a single heartbeat and/or a mathematical combination (e.g., mean, median, etc.) for an ensemble of heart beats. The table indicates examples for statistical distribution of the voltage levels plotted in FIG. 4A.

In accordance with new and unique aspects herein, it has been found that, as evidenced in FIG. 4A, when LV pacing achieves capture or fusion during one heart beat or an ensemble of heart beats, the associated baseline voltage prior to LV pacing during the next heart beat or ensemble is consistently within a relatively small range centered about 0 mV. For example, the capture sub-collection of heart beats in group 402 exhibited a voltage level distribution with a mean of 0.35 mV with a standard deviation of +/−0.33 mV, a range of −0.27 mV to 1.19 mV and a median of 0.31 mV. As another example, the fusion sub-collection of heart beats in group 404 exhibited a voltage level distribution with a mean of 0.15 mV with a standard deviation of +/−0.23 mV, a range of −0.25 mV to 0.44 mV and a median of 0.21 mV.

In contrast, when LV pacing is ineffective and results in pseudofusion during one heart beat or an ensemble of heart beats, the associated baseline voltage prior to LV pacing during the next heart beat or ensemble is widely variable, but consistently at a voltage outside of the range associated with capture and fusion. For example, the pseudofusion sub-collection of heart beats in group 406 exhibited a voltage level distribution with a mean of 3.06 mV with a standard deviation of +/−5.64 mV, a range of −19.5 mV to 12.9 mV and a median of 3.19 mV.

Figure 4B:
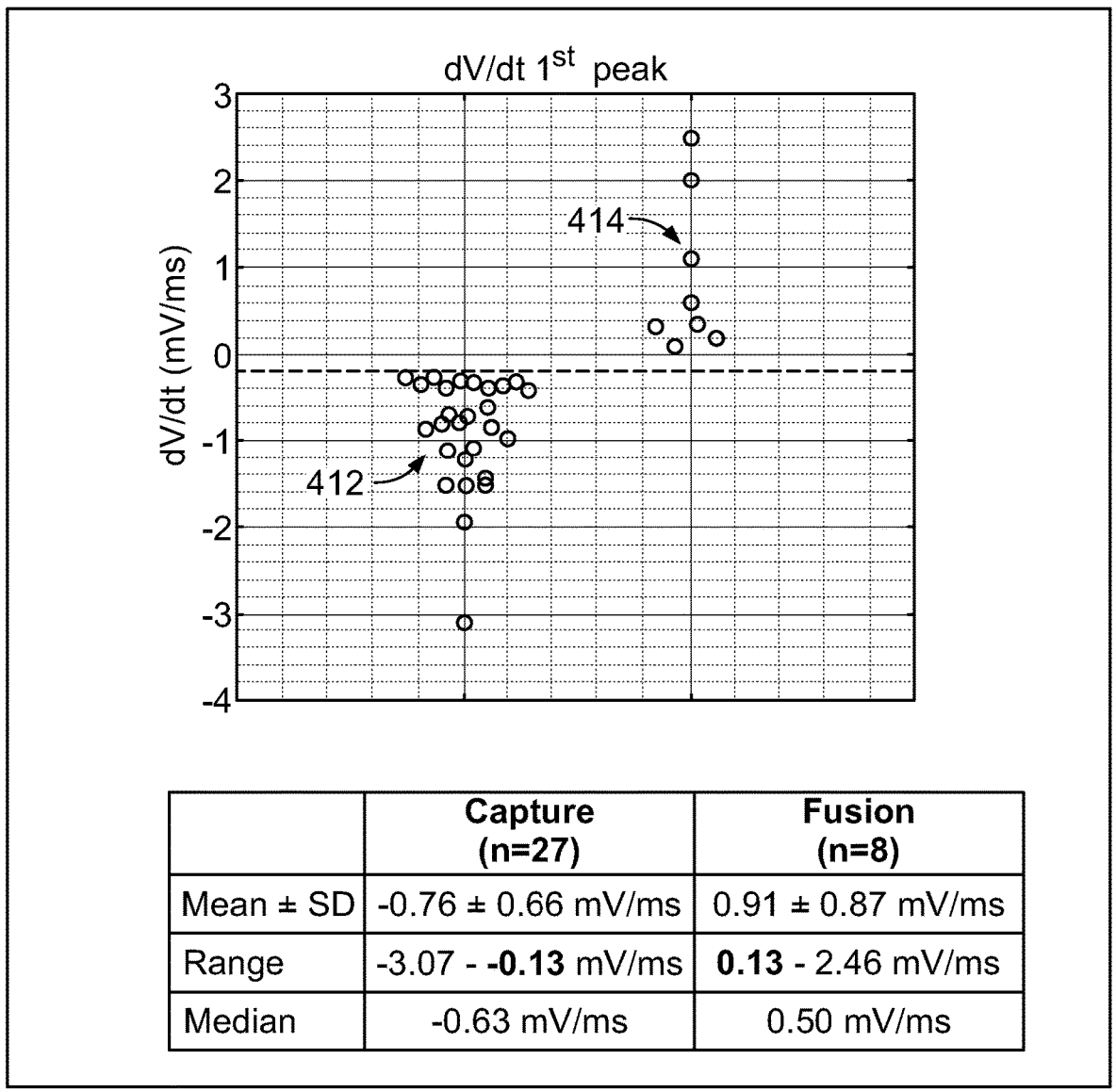
FIG. 4B illustrates a plot of values measured for peak voltage slope (e.g., dV/dt) experienced during a post-pacing window for collections of heart beats associated with the various types of myocardial activation in accordance with embodiments herein.

FIG. 4B illustrates a plot of values measured for peak voltage slope (e.g., dV/dt) experienced during a post-pacing window for collections of heart beats associated with the various types of myocardial activation. The points in FIG. 4B may represent data collected from the same patient population as in FIG. 4A. The points in FIG. 4B correspond to a first identified peak in the slope of the CA signals following an LV pacing event. Each point in FIG. 4B corresponds to a single heart beat or an ensemble of heart beats exhibiting a common MA. For example, the group 412 represents a sub-collection of heart beats/ensembles during which the patient(s) experience LV capture. The group 414 represents a sub-collection of heart beats/ensembles during which the patient(s) experienced fusion following a corresponding group of LV paced events.

A table is presented below the peak voltage slope plot of FIG. 4B. While FIG. 4B does not include a peak voltage slope plot for pseudofusion, optionally a peak voltage slope plot may be determined for pseudofusion and utilized as additional criteria to differentiate between the types of MA. A data point may represent a single heart beat and/or a mathematical combination (e.g., mean, median, etc.) for an ensemble of heart beats. The table indicates examples for statistical distribution of the peak voltage slopes plotted in FIG. 4B.

In accordance with new and unique aspects herein, it has been found that, as evidenced in FIG. 4B, when LV pacing achieves capture during one heart beat or an ensemble of heart beats, the associated peak voltage slope has a negative sign and is consistently within a relatively medium range centered about a negative voltage per millisecond. For example, the capture sub-collection of heart beats in group 412 exhibited a voltage level distribution with a mean of −0.76 mV/ms with a standard deviation of +/−0.66 mV/ms, a range of −3.07 mV/ms to −0.13 mV/ms and a median of −0.63 mV/ms.

In contrast, when LV pacing results in fusion, the associated peak voltage slope has a positive sign and is consistently within a medium range centered about a positive voltage per millisecond. For example, the fusion sub-collection of heart beats in group 414 exhibited a peak voltage slope distribution with a mean of 0.91 mV/ms with a standard deviation of +/−0.87 mV/ms, a range of 0.13 mV/ms to 2.46 mV/ms and a median of 0.50 mV/ms.

Figure 5:
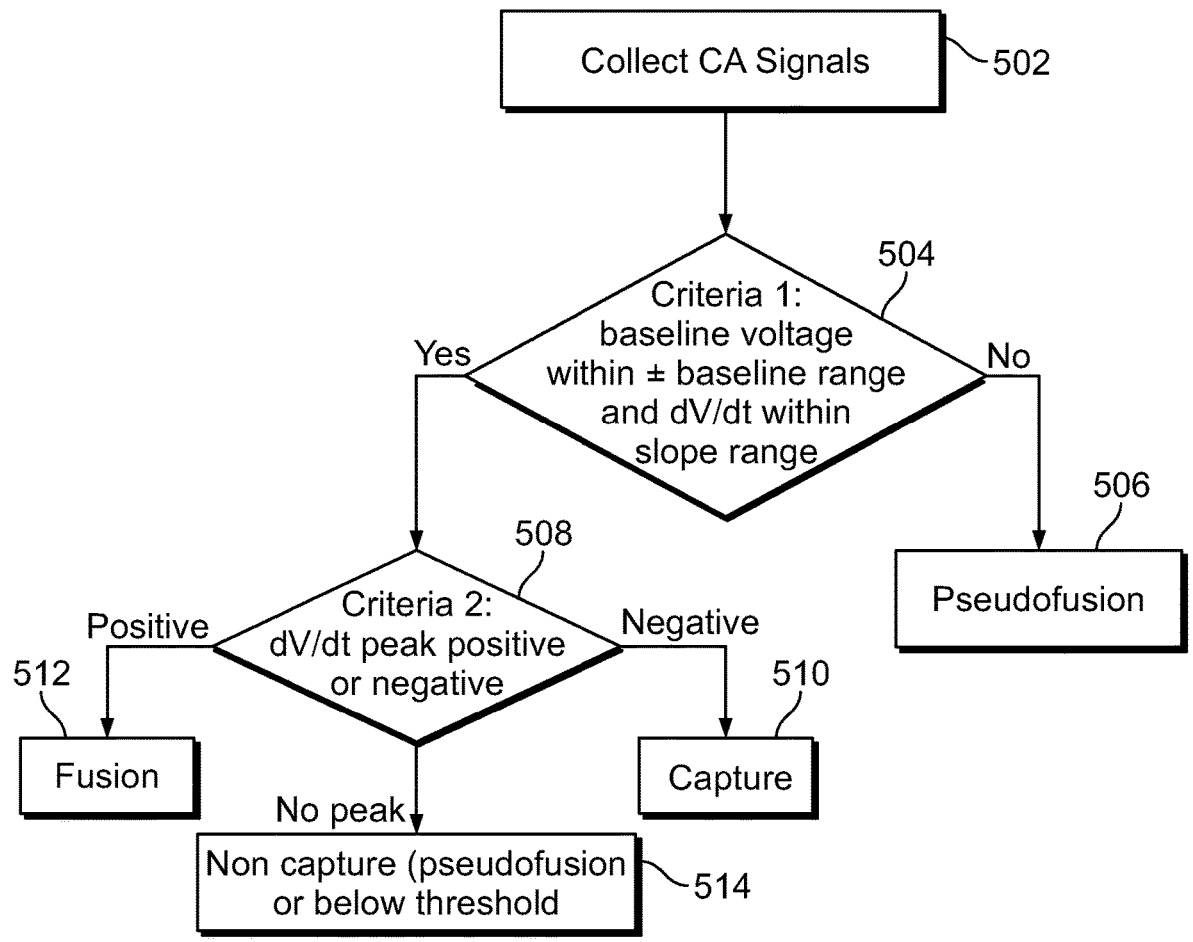
FIG. 5 illustrates a process for differentiating between MA capture types in accordance with embodiments herein.

FIG. 5 illustrates a process for differentiating between MA capture types in accordance with embodiments herein. The operations of FIG. 5 may be implemented wholly or in part by one or more processors, firmware and hardware within an IMD. Additionally or alternatively, the data collection operations of FIG. 5 may be implemented by an IMD and/or surface ECG electrodes, while the remaining analysis operations of FIG. 5 may be implemented by next device, such as a local external device (e.g., a bedside monitor, smart phone, tablet computer, etc.), and/or a remote server. Additionally or alternatively, a portion of the analysis operations may be implemented by the processors, firmware and hardware within an IMD, while remaining portion of the analysis operations are implemented by a local external device and/or remote server.

At 502, CA signals are collected along one or more sensing vectors, where the CA signals are at least indicative of ventricular activity, and optionally additionally indicative of atrial activity. The CA signals are at least partially collected from a sensing vector representing an LV-RV transverse sensing vector. By way of example, the LV-RV transverse sensing vector then be defined between an LV electrode and an RV electrode (e.g., an RV coil or tip electrode). As a further example, the LV electrode may be defined to be the cathode while the RV coil is defined to be the anode, such as in connection with an IMD operating as a CRT-D device. As another example, the LV electrode may be defined to be the cathode, while the RV ring electrode is defined to be the anode, such as in connection with an IMD operating as a CRT-P device.

In the event an LV lead is utilized having multiple LV electrodes provided thereon, the sensing vector may utilize a one of the LV electrodes designated as the LV pacing electrode. Optionally, when more than one LV electrode is utilized for pacing, and the pacing is delivered in a successive manner, the sensing vector may utilize the one of the LV electrodes that are designated to be the first LV pacing site. Optionally, when more than one LV electrode is utilized for pacing and pacing is delivered simultaneously from the combination of LV electrodes, one, a subset or all of the LV electrodes utilized for simultaneous pacing may be also utilized for sensing.

In accordance with new and unique aspects herein, it has been found that certain sensing vectors are better suited to detect interaction of intrinsic and paced activity in certain therapy configurations. For example, it has been found that a localized unipolar sensing vector from the LV pacing site to an RV electrode collects information of interest regarding a combination of intrinsic and paced activity along the left and right sides of the septal wall, namely an intrinsic incoming wave front along the RV side of the septal wall, as well as the ER wavefront along the LV side of the septal wall.

Continuing with the foregoing example, if the only sensing channel was implemented with LV electrodes formed in a bipolar sensing configuration, the LV bipolar sensing vector would be less sensitive or insensitive to intrinsic activity traveling down the right side of the septal wall along the RV. If the only sensing channel was implemented with RV electrodes formed a bipolar sensing configuration, the RV bipolar sensing vector would be less or insensitive to ER activity traveling down the left side of the septal wall along the LV.

Optionally, the CA signals may be collected utilizing primary and secondary sensing channels. The primary sensing channel may be defined by one or more LV electrodes in a manner oriented to collect intrinsic and ER based wave front propagating along the left side septal wall. A secondary sensing channel may be defined between one or more combinations of secondary electrodes, where the secondary sensing vector is aligned to be sensitive to intrinsic activity traveling down the right side of the septal wall. When a separate secondary sensing vector is provided to collect intrinsic activity along the RV side of the septal wall, optionally, a bipolar sensing configuration may be utilized for one or both of the primary and secondary sensing channels.

At 504, one or more processors analyze the CA signals to identify and compare one or more MA COI relative to a first MA criteria. For example, the one or more processors may analyze the CA signals to identify baseline voltage occurring during the pre-LV window. To identify the baseline voltage, the one or processors position a pre-LV window to start at a predetermined point in time before a next scheduled LV pacing event and/or to start at a predetermined point in time following a most recent intrinsic or paced atrial event. For example, the pre-LV window may have a duration of 10 ms that is timed to begin 10 ms immediately preceding the next scheduled LV pacing event. The one or more processors analyze the CA signals collected over the LV-RV transverse sensing vector during the pre-LV window to identify the baseline voltage and the baseline slope. The one or more processors may determine, as the baseline voltage, the mean, median, negative peak, positive peak, peak to peak variation or other mathematical representation of the voltage level of the CA signal over the pre-LV window.

Additionally, the one or more processors analyze the CA signals to identify a baseline slope occurring during the pre-LV window. The pre-LV window utilized to determine the baseline slope baby the same or different pre-LV window when utilized to determine the baseline voltage. For example, the pre-LV window for the baseline voltage and slope may be common. Alternatively, the baseline slope may be determined from a pre-LV window that may begin before or after the beginning of the pre-LV window utilized for the baseline voltage. Alternatively, the pre-LV window utilized for the baseline slope may have a longer duration than the pre-LV window utilized for the baseline voltage. To identify the baseline slope, the one or more processors identify the derivative of the CA signal continuously or at discrete points along the CA signal over the pre-LV window. The one or more processors may determine the peak negative or positive derivative to represent the baseline slope. Additionally or alternatively, the one or more processors may determine the baseline slope to correspond to the mean, median or other mathematical representation of the derivative of the CA signals over the pre-LV window.

As part of the first MA criteria analysis, the one or more processors compare the baseline voltage to a baseline voltage range and compare the baseline slope to a baseline slope range. The baseline voltage and slope ranges may be pre-programmed by a clinician at the time of implant and/or at various times throughout the useful life of the IMD. Additionally or alternatively, the baseline slope and voltage ranges may be automatically determined and updated by the IMD, such as during a calibration operation that may be performed by the IMD automatically throughout the useful life.

When one or both of the baseline voltage and/or slope are outside of the corresponding baseline voltage and/or slope range, flow moves to 506. At 506, the one or more processors designate a current heartbeat and/or series of heartbeats to have a pseudofusion type. For example, the one or more processors may update a log or other record tracking a number of pseudofusion beats.

Alternatively, at 504, when the baseline voltage and slope are both within the corresponding baseline voltage and slope ranges, flow moves to 508. When flow moves to 508, the process has determined that the current beat and/or series of beats are one of at least two types, namely fusion or capture beats.

At 508, one or more processors analyze the CA signals to identify and compare one or more MA COI relative to a second MA criteria. For example, the one or more processors may analyze the CA signals to identify a post-LV pacing event peak slope sign occurring during the post-LV window. The one or processors position a post-LV window to start at a predetermined point in time following a most recent LV pacing event. For example, the post-LV window may begin approximately 20 ms after the LV pacing event and continue until approximately hundred and 50 ms after the LV pacing event, thereby defining a post LV window of approximately 130 ms. The one or more processors analyze the CA signals collected over the LV-RV transverse sensing vector during the post-LV window to identify the peak slope sign. The one or more processors may determine, as the peak slope sign, maximum value of the derivative of the CA signals during the post-LV window. Additionally or alternatively, the peak slope sign may represent a mean, median, or other mathematical representation of the derivative of the CA signal over the post-LV window.

As part of the second MA criteria analysis, the one or more processors determine whether the peak slope sign is positive or negative. When the peak slope sign is positive, flow moves to 512. When the peak slope sign is negative, flow moves to 510. In accordance with new and unique aspects herein, it is been found that the sign of the peak slope during the post-LV window affords a strong differentiator between the fusion and capture MA types. Accordingly, at 510, the one or more processors designate a current heartbeat and/or series of heartbeats to have a capture type and/or to be a capture beat(s). For example, the one or more processors may update a log or other record tracking a number of capture beats. At 512, the one or more processors designate a current heartbeat and/or series of heartbeats to have a fusion type and/or to be a fusion beat. For example, the one or more processors may update a log or other record tracking a number of fusion beats.

In addition at 508, the potential exists that the CA signals during the post-LV window will not exhibit a peak slope. When no peak is identified at 508, flow moves to 514. At 514, the one or more processors designate the current beat and/or series of beats to have a pseudofusion type and/or to be a pseudofusion beat, and may accordingly update the log or other record tracking the number of pseudofusion beats. At 514, the one or more processors may store in the memory, at least one of: i) a histogram indicating a relation between a number of beats during which LV pacing was delivered and a number of the beats for which the LV pacing was effective to achieve at least one of capture or fusion; ii) a log of at least one of a number of capture beats, number of fusion beats or number of pseudofusion beats; iii) a log of a percentage of a total number of LV paced beats for which the LV pacing pulses achieved capture; iv) a log of a percentage of a total number of LV paced beats for which the LV pacing pulses achieved fusion; or v) a log of a percentage of a total number of LV paced beats for which the LV pacing pulses achieved pseudofusion.

In accordance with the foregoing process, an automated algorithm is described that distinguishes among the 3 pacing scenarios described above using the LV pacing electrode EGM. Morphological features in the CA signals captured over an LV-RV sensing vector are used to assess the pacing mechanism. The EGM features used are: i) Baseline EGM voltage pre-LV pacing; 2) Baseline EGM dV/dt pre-LV pacing; and 3) EGM dV/dt peak post-LV pacing.

Figure 6:
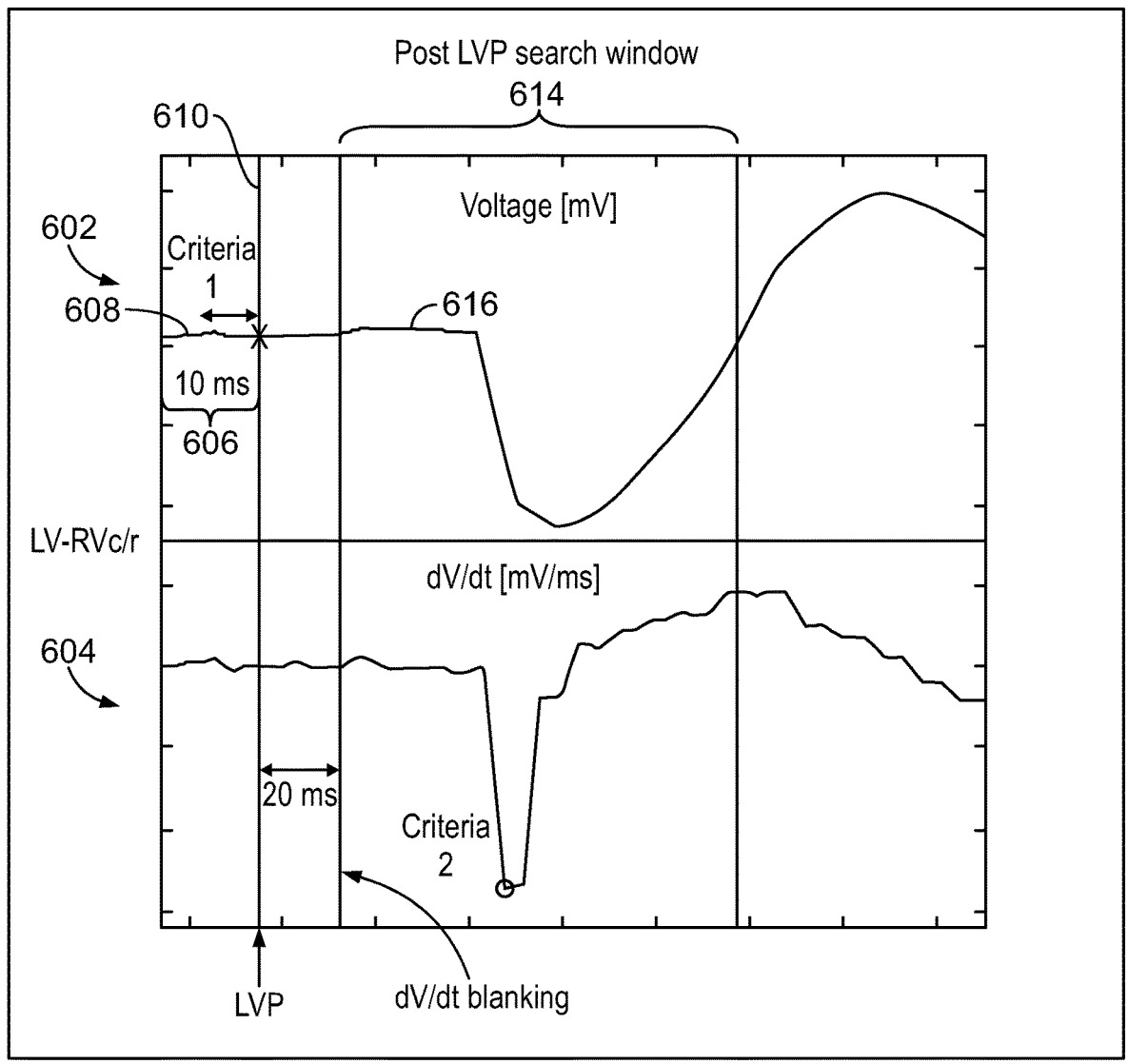
FIG. 6 illustrates an example of CA signals for one heart beat collected along a LV-RV sensing vector (e.g., collected from the LV pacing cathode—RV coil (or RV ring)) in accordance with embodiments herein.

FIG. 6 illustrates an example of CA signals for one heart beat collected along a LV-RV sensing vector (e.g., collected from the LV pacing cathode-RV coil (or RV ring)). The upper panel 602 illustrates the voltage level of the CA signal over the heart beat, while the lower panel 604 illustrates the derivative/slope of the same CA signal. With reference to the upper panel 602, in connection with the first MA criteria, a pre-LV window 606 is overlaid upon a first portion 608 of the CA signals. For the example, the pre-LV window 602 has a duration of 10 ms and is positioned to occur immediately before a scheduled LV pacing pulse (denoted by the line at 610). The one or more processors determine the mean baseline voltage and determine whether the mean baseline voltage is within the baseline voltage range (e.g., ±1.2 mV). The one or more processors further determine the mean baseline slope and determine whether the mean baseline slope is within the baseline slope range (e.g., ±0.1 mV/ms). If either the baseline voltage or baseline slope are not within the established limits, the pacing impulse is classified as pseudofusion. If both of the baseline voltage and slope are within the established limits, the analysis moves to the second MA criteria for further adjudication.

With reference to the lower panel 604, in connection with the second MA criteria, a post-LV window 614 is overlaid upon a second portion 616 of the CA signals. For example, the post-LV window may extend between 20 ms and 150 ms after the LV pacing pulse. The one or more processors identify the first positive or negative slope (e.g., dV/dt) peak that is greater than a select level (e.g., ±0.1 mV/ms). If the peak identified is negative, the LV pacing event is classified as capture. If the peak is positive, the LV pacing event is classified as fusion. Otherwise, if there is no peak identified, the LV pacing event is classified as pseudofusion.

The process of FIG. 5 may be continuously performed by an IMD, local external device and/or remote server.

Figure 7:
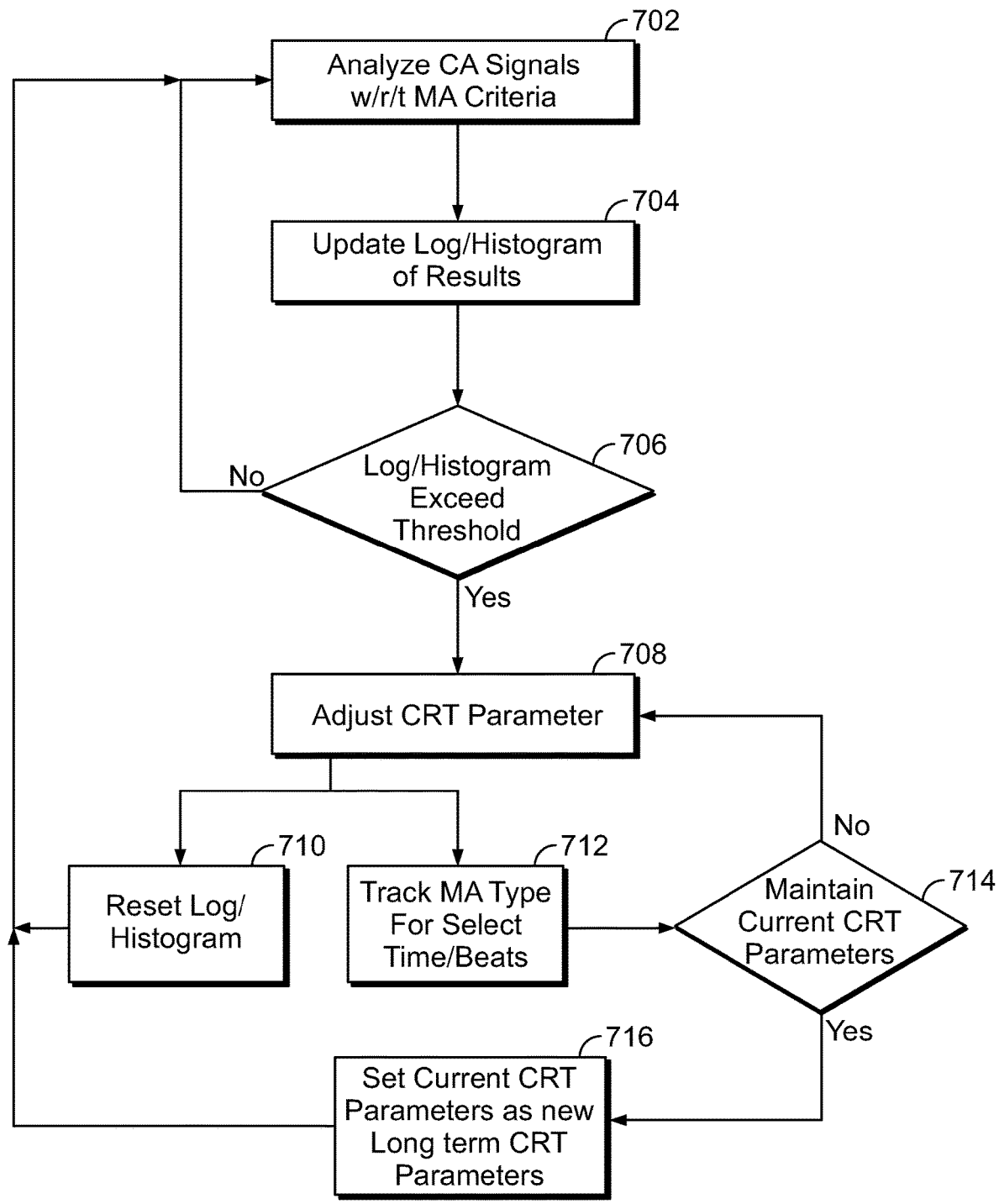
FIG. 7 illustrates a process for updating CRT parameters based on the results of the MA type tracking in accordance with embodiments herein.

FIG. 7 illustrates a process for updating CRT parameters based on the results of the MA type tracking in accordance with embodiments herein. The process of FIG. 7A be implemented in whole or in part by one or a combination of one or more IMDs, a local external device, a clinician's programmer and/or remote server. At 702, the one or more processors analyze CA signals with respect to at least first and second MA criteria in accordance with one or more of the embodiments described herein. At 704, the one or more processors store the results of the analysis and update one or more logs and/or histogram tracking the various beat type aspects are described herein. For example, the results may be stored in one or more of i) a histogram indicating a relation between a number of beats during which LV pacing was delivered and a number of the beats for which the LV pacing was effective to achieve at least one of capture or fusion; ii) a log of at least one of a number of capture beats, number of fusion beats or number of pseudofusion beats; iii) a log of a percentage of a total number of LV paced beats for which the LV pacing pulses achieved capture; iv) a log of a percentage of a total number of LV paced beats for which the LV pacing pulses achieved fusion; or v) a log of a percentage of a total number of LV paced beats for which the LV pacing pulses achieved pseudofusion.

At 706, the one or more processors determine whether one or more aspects of the results exceed one or more thresholds. For example, the processors may determine whether the number of pseudofusion beats has exceeded a threshold. When the pseudofusion beat count does not exceed the threshold, flow returns to 702 and the tracking process continues. When the pseudofusion beat count does exceed the threshold, the process determines that the current CRT parameters are not achieving a desired level of efficiency and flow moves to 708.

At 708 to 716, the process seeks to automatically determine new CRT parameters that are more effective at achieving capture and/or fusion. At 708, the one or more processors adjust one or more CRT parameters, such as setting a candidate AV delay and/or candidate VV delay. Thereafter, flow may branch in one or both of multiple directions to 710 and 712. When flow branches to 710, the one or more processors reset one or more of the counts maintained in the log or histogram. For example, all of the capture, fusion and pseudofusion counts may be reset. Optionally, the pseudofusion count may be reset, but not the capture and fusion counts. Optionally, any combination of the counts may be reset, while any combination of the counts is continued. Flow returns from 710 to 702, where the process is repeated. Optionally, the operation at 710 may be omitted entirely.

Additionally or alternatively, flow moves to 712. At 712, the one or more processors make an initial adjustment of one or more candidate CRT parameters, such as the candidate AV delay and/or candidate VV delay. At 712, the one or more processors use the new candidate CRT parameter values for a select period of time or beats while tracking the MA types that occur during each beat. For example, the process of FIG. 5 is repeated for the select period of time or beats while the log and/or histogram of MA types is updated. After the desired number of beats or time, flow moves to 714. At 714, the one or more processors analyze the logs and/or histograms to determine whether the count for one or more of the MA types exceeds a corresponding threshold. For example, it may be determined that 75% of the LV pacing pulses achieved capture or fusion and thus the current candidate CRT parameter settings are deemed efficient enough to be utilized for long term operation of the IMD. Additionally or alternatively, the process may determine that X total or Y percentage of the beats were pseudofusion beats, or that 3 out of every 10 beats were pseudofusion beats, or another metric may be used to track pseudofusion beats. When a sufficient number of the beats exhibit pseudofusion, the process determines that the current candidate CRT parameters are not sufficiently effective and thus flow moves to 708. At 708, the one or more processors adjust one or more of the candidate CRT parameters which are used for a desired number of beats or time to track MA types at 712. The process at 708, 712, 714 repeats until the tracking indicates that the current candidate CRT parameters are achieving a desired number of capture and/or fusion beats. Thereafter, flow moves to 716, where the current candidate CRT parameters are stored to be used as the long term resultant CRT parameters. For example, a candidate set of CRT parameters may be moved to a long term storage register as resultant CRT parameters.

The process of FIG. 7 may be implemented automatically by the IMD and/or an external device periodically or based on certain trigger criteria (e.g., a select number of pseudofusion beats). Additionally or alternatively, the process of FIG. 7 may be implemented under control of a clinician through a programmer device. The clinician may make the determinations and adjustments at 706, 708, 712, and 714.

In accordance with the above described embodiments, methods and systems are described for designating between types of activation by a pulse generator configured to deliver a left ventricular (LV) pacing pulse at an LV pacing site as part of a cardiac resynchronization therapy (CRT), comprising: a sensing channel configured to collect cardiac activity (CA) signals along at least one sensing vector extending through a septal wall between the LV and right ventricle (RV), the CA signals indicative of one or more beats, the CA signals including a pre-LV pacing segment indicative of cardiac activity preceding the LV pacing pulse and a post-LV pacing segment indicative of cardiac activity following the LV pacing pulse; memory to store program instructions; one or more processors configured to implement the program instructions to perform: analyze the pre-LV pacing segment to identify a first myocardium activation (MA) characteristic of interest (COI); analyze the post-LV pacing segment to a second MA COI; compare the first and second MA COI to first and second MA criteria, respectively; designate the CA signals to be indicative of one of a fusion beat, a capture beat or a pseudofusion beat based on the comparison of the first and second MA COI to first and second MA criteria; and store a result of the designation.

In accordance with embodiments herein, the logs, histograms and other results collected herein may be utilized in various manners. For example, the results may be utilized to identify the amount of pacing that is effectively delivered. For example, the results at 151, 153 may include a count (or histogram) of the percent pacing delivered with a counter (or histogram) of the captured pacing (capture/fusion). As a nonlimiting example, the results may indicate that over a predetermined period of time, the patient was paced 98% of the time, of which 95% of the paced events achieved effective capture. The results may further differentiate between beats in which capture was achieved, versus fusion (e.g., 70% capture, 30% fusion).

In accordance with embodiments herein, the results may be analyzed at a local external device, clinician programmer, a remote server or other external processing device to, among other things, provide guidance for adjusting the CRT parameters to improve/optimize a CRT therapy. For example, the results may be manually or automatically analyzed to identify the MA type and determine when a pseudofusion count is higher than a desired (e.g., threshold) level. When the pseudofusion count succeed a desired level, the external device may automatically adjust the AV (or VV) delay in increments until achieving a desired number of capture or fusion beats.

Additionally or alternatively, the IMD may automatically adjust CRT parameters when an undesirably high number of pseudofusion beats are identified. For example, a pseudofusion threshold may be programmed by a clinician into the memory 152 of the IMD. The MA monitor 170 may track the count of pseudofusion beats. When the count of pseudofusion beats exceeds the threshold, the CRT control 166 may implement a CRT parameter update process. In the CRT parameter update process, the CRT control 166 may increment a lead adjust CRT parameters, such as the AV delay and/or VV delay. The AV delay and/or VV delay may be incremented by a predetermined amount or percentage. With the new AV delay and/or VV delay, the IMD may reset one or more counters in the log or histogram 153. The new AV delay and/or VV delay may be utilized for a period of time until a new count of pseudofusion beats exceeds a threshold. When the pseudofusion beats exceeds the threshold, the IMD may again adjust the AV delay and/or VV delay. This process may be iteratively repeated until a combination of CRT parameters are identified that do not cause pseudofusion beats in excess of a threshold amount within a predetermined period of time (e.g., X pseudofusion beats over a one-day period).

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as distinguishes, and are not intended to impose numerical requirements on their objects or order of execution on their acts.

What is claimed is:

1. A system for designating between types of activation by a pulse generator included with an implantable medical device (IMD) as part of a cardiac resynchronization therapy (CRT), comprising:
   a pulse generator configured to deliver a left ventricle (LV) pacing pulse at an LV pacing site as part of the CRT;
   a sensing channel configured to collect cardiac activity (CA) signals along at least one sensing vector extending through a septal wall between the LV and right ventricle (RV), the CA signals indicative of one or more beats, the CA signals including a pre-LV pacing segment indicative of cardiac activity preceding the LV pacing pulse and a post-LV pacing segment indicative of cardiac activity following the LV pacing pulse;
   memory, included with the IMD, to store program instructions, an atrial-ventricular delay parameter utilized by the CRT, and a ventricular ventricular delay parameter utilized by the CRT;
   one or more processors, included with the IMD, configured to implement the program instructions to perform:
      analyze the pre-LV pacing segment to identify a first myocardium activation (MA) characteristic of interest (COI);
      analyze the post-LV pacing segment to identify a second MA COI;
      compare the first and second MA COI to first and second MA criteria, respectively, wherein the first and second MA criteria are stored in the memory,
   wherein the first MA criteria is a characteristic corresponding to the first MA COI occurring during the pre-LV pacing segment;
      designate the CA signals to be indicative of one of a fusion beat, a capture beat or a pseudofusion beat based on the comparison of the first and second MA COI to the first and second MA criteria;
      store a result of the designation;
      based on the result of the designation of the CA signals, adjust at least one of the atrial-ventricular delay parameter or the ventricular ventricular delay parameter utilized by the CRT; and
      deliver the CRT by the pulse generator.

2. The system of claim 1, wherein the first MA COI is indicative of whether LV tissue proximate to the LV pacing site is in a state that is responsive to the LV pacing pulse.

3. The system of claim 1, wherein the one or more processors analyze the pre-LV pacing segment of the CA signals to identify, as the first MA COI, at least one of a baseline voltage or baseline slope, the one or more processors configured to compare the at least one of the baseline voltage or baseline slope to a corresponding baseline voltage range or baseline slope range which represents the first MA criteria.

4. The system of claim 3, wherein at least one of the baseline voltage range or baseline slope range define a limit in order for LV tissue proximate to the LV pacing site to be in a non-refractory state.

5. The system of claim 3, wherein the one or more processors are further configured to designate the CA signals as a pseudofusion beat when the comparison of the first MA COI to the first MA criteria indicates that the LV tissue is in a refractory state that is nonresponsive to the LV pacing pulse.

6. The system of claim 3, wherein the one or more processors are further configured to designate the CA signals as at least one of a capture beat or a fusion beat when the comparison of the first MA COI to the first MA criteria indicates that the LV tissue is in a non-refractory state that is responsive to the LV pacing pulse.

7. The system of claim 1, wherein the second MA COI is further indicative of whether the LV pacing pulse achieved capture or fusion and wherein the first MA COI is further indicative of whether the CA signals indicate the pseudofusion beat.

8. The system of claim 1, wherein the one or more processors are configured to analyze the post-LV pacing segment of the CA signals to identify, as the second MA COI, a sign of an initial slope of an evoked response (ER) that is responsive to the LV pacing pulse.

9. The system of claim 8, wherein the one or more processors are further configured to designate the CA signals as a fusion beat when the sign of the initial slope is positive and to designate the CA signals as a capture beat when the sign of the initial slope is negative.

10. The system of claim 8, wherein the one or more processors are further configured to identify the sign of a peak in the initial slope, and to designate the CA signals as a pseudofusion beat when no peak is identified in the post-LV pacing segment of the CA signals.

11. The system of claim 1, wherein, based on the result of the designation, the one or more processors are further configured to generate and the memory is configured to store at least one of:
   i) a histogram indicating a relation between a number of beats during which LV pacing was delivered and a number of the beats for which the LV pacing was effective to achieve at least one of capture or fusion;
   ii) a log of at least one of a number of capture beats, number of fusion beats or number of pseudofusion beats;
   iii) a log of a percentage of a total number of LV paced beats for which the LV pacing pulses achieved capture;
   iv) a log of a percentage of a total number of LV paced beats for which the LV pacing pulses achieved fusion; or
   v) a log of a percentage of a total number of LV paced beats for which the LV pacing pulses achieved pseudofusion.

12. The system of claim 1, wherein the one or more processors are further configured to adjust at least one of the atrial-ventricular delay or the ventricular ventricular delay parameter utilized by the CRT when a count of the pseudofusion beats exceeds a threshold stored in the memory.

13. A method for designating between types of activation in connection with cardiac resynchronization therapy (CRT) that includes delivery of a left ventricle (LV) pacing pulse at an LV pacing site, comprising:
   under control of one or more processors within an implantable medical device (IMD),
   collecting cardiac activity (CA) signals along at least one sensing vector extending through a septal wall between the LV and right ventricle (RV), the CA signals indicative of one or more beats, the CA signals including a pre-LV pacing segment indicative of cardiac activity preceding the LV pacing pulse and a post-LV pacing segment indicative of cardiac activity following the LV pacing pulse;

analyzing the pre-LV pacing segment to identify a first myocardium activation (MA) characteristic of interest (COI);

analyzing the post-LV pacing segment to identify a second MA COI;

comparing the first and second MA COI to first and second MA criteria, respectively, wherein the first MA criteria is a characteristic corresponding to the first MA COI occurring during the pre-LV pacing segment;

designating the CA signals to be indicative of one of a fusion beat, a capture beat or a pseudofusion beat based on the comparison of the first and second MA COI to the first and second MA criteria;

storing a result of the designating;

based on the result of the designation of the CA signals, adjusting at least one of an atrial-ventricular delay parameter or a ventricular ventricular delay parameter utilized by the CRT; and delivering the CRT.

14. The method of claim 13, wherein the first MA COI is indicative of whether LV tissue proximate to the LV pacing site is in a state that is responsive to the LV pacing pulse.

15. The method of claim 13, wherein the analyzing the pre-LV pacing segment of the CA signals includes identifying, as the first MA COI, at least one of a baseline voltage or baseline slope; and the comparing includes comparing the at least one of the baseline voltage or baseline slope to a corresponding baseline voltage range or baseline slope range which represents the first MA criteria.

16. The method of claim 15, wherein at least one of the baseline voltage range or baseline slope range define a limit in order for LV tissue proximate to the LV pacing site to be in a non-refractory state.

17. The method of claim 15, wherein the designating further includes designating the CA signals as a pseudofusion beat when the comparison of the first MA COI to the first MA criteria indicates that the LV tissue is in a refractory state that is nonresponsive to the LV pacing pulse; and further includes designating the CA signals as at least one of a capture beat or a fusion beat when the comparison of the first MA COI to the first MA criteria indicates that the LV tissue is in a non-refractory state that is responsive to the LV pacing pulse.

18. The method of claim 13, wherein the second MA COI is further indicative of whether the LV pacing pulse achieved capture or fusion and wherein the first MA COI is further indicative of whether the CA signals indicate the pseudofusion beat.

19. The method of claim 13, wherein the analyzing includes analyzing the post-LV pacing segment of the CA signals to identify, as the second MA COI, a sign of an initial slope of an evoked response (ER) that is responsive to the LV pacing pulse.

20. The method of claim 19, wherein the designating further includes designating the CA signals as a fusion beat when the sign of the initial slope is positive and designating the CA signals as a capture beat when the sign of the initial slope is negative.

21. The method of claim 13, further comprising delivering the CRT utilizing LV only pacing.

22. The method of claim 13, further comprising storing at least one of:
   i) a histogram indicating a relation between a number of beats during which LV pacing was delivered and a number of the beats for which the LV pacing was effective to achieve at least one of capture or fusion;
   ii) a log of at least one of a number of capture beats, number of fusion beats or number of pseudofusion beats;
   iii) a log of a percentage of a total number of LV paced beats for which the LV pacing pulses achieved capture;
   iv) a log of a percentage of a total number of LV paced beats for which the LV pacing pulses achieved fusion; or
   v) a log of a percentage of a total number of LV paced beats for which the LV pacing pulses achieved pseudofusion.

23. The method of claim 13, based on the result of the designation, further comprising:
   determining a count of pseudofusion beats; and
   adjusting at least one of the atrial-ventricular delay or the ventricular ventricular delay parameter utilized by the CRT when the count of pseudofusion beats exceeds a threshold.

* * * * *